United States Patent [19]

Cardarelli

[11] 4,166,111
[45] Aug. 28, 1979

[54] METHOD AND COMPOSITION FOR THE LONG TERM CONTROLLED RELEASE OF A NON-PERSISTENT ORGANOTIN PESTICIDE FROM AN INERT MONOLITHIC THERMOPLASTIC MATERIAL

[75] Inventor: Nathan F. Cardarelli, Barberton, Ohio

[73] Assignee: Environmental Chemicals, Inc., Barrington, Ill.

[21] Appl. No.: 916,570

[22] Filed: Jun. 19, 1978

[51] Int. Cl.$^2$ ............................................. A01N 9/00
[52] U.S. Cl. ....................................... 424/78; 424/83; 424/288
[58] Field of Search ............................ 424/78, 288, 83

[56] References Cited

U.S. PATENT DOCUMENTS

| | | | |
|---|---|---|---|
| 3,234,032 | 2/1966 | Leebrick et al. | 424/288 X |
| 3,236,793 | 2/1966 | Robins et al. | 424/288 X |
| 3,417,181 | 12/1968 | Cardarelli | 424/229 |
| 3,590,119 | 6/1971 | Cardarelli et al. | 424/22 |
| 3,639,583 | 2/1972 | Cardarelli et al. | 424/125 |
| 4,012,347 | 3/1977 | Ohlitz et al. | 424/288 X |

OTHER PUBLICATIONS

Chemical Abstracts 75:97577c (1971).

Primary Examiner—Leonard Schenkman
Attorney, Agent, or Firm—Oldham, Oldham, Hudak & Weber

[57] ABSTRACT

A method and composition for destroying pest insects in their aquatic stage and other pest-life forms over a sustained period of time, by the gradual and continuous release of an organotin substance from an inert thermoplastic medium. The composition comprises an organotin of extremely low water solubility bound in an ethylene vinyl acetate copolymer, in which said organotin is insoluble and in which said organotin is uniformly dispersed with an inert coleachant of moderate to low water solubility. When this formulation is brought into contact with water, the coleachant gradually solvates into the water creating and enhancing the development of porosity within the thermoplastic phase. Said organotin agent, interspersed within the thermoplastic matrix, contacts the entering water and egresses as molecular aggregates being washed through the pore system and into the external watery medium. Such aggregates being toxic to mosquito larva, other insects and various other pesteferous life forms, upon continuous exposure, leads to a condition of terminal chronic intoxication.

18 Claims, No Drawings

METHOD AND COMPOSITION FOR THE LONG TERM CONTROLLED RELEASE OF A NON-PERSISTENT ORGANOTIN PESTICIDE FROM AN INERT MONOLITHIC THERMOPLASTIC MATERIAL

BACKGROUND OF THE INVENTION

This invention relates to certain trialkyl and triaryl organotins and their dissemination in a continuous and controlled manner into water courses infested with mosquito larva and other susceptible aquatic pest life. Mosquito larva develops through morphogenetic stages in water, emerging in time as adults capable of transmitting dreaded diseases which include encephalitis, malaria, yellow fever, and the like, as well as creating a nuisance to man and man's domestic cattle by their proclivity towards biting and other annoyances. Similarly, other insecta, such as flies of the Simulium family, spend their larval stages in water, emerging as adults capable of transmitting onchocerciasis, a dreaded parasitic disease manifested as blindness in exposed human populaces. Snail hosts of parasitic trematodes, as well as the trematode larva, likewise, dwell in water and can similarly be controlled using the invention described in this specification.

Insects and other bearers of disease are normally and conventionally destroyed through treating the infested waters with larvicidal agents or saturating the air with sprays, fogs, droplets, etc., of specified toxic substances. It is well known that the conventional methodology provides but temporary relief, while of necessity, the use of toxicant concentrations has, as a rule, a significant detrimental ecological effect on non-target organisms, soil, air and water. As described in the monumental text by Cardarelli, 1976, and is now well known to the pesticide formulation and used in the art, through the incorporation of select pesticides in select polymeric matrices, it is possible to cause a slow-long duration release of ultralow concentrations of said pesticides in the pest-infested environment with efficacious benefit and much reduced environmental impact. When target organisms are continuously exposed to very low toxicant concentrations, such concentrations being far too small to materially affect insect control, the gradual accumulation of such agents in the pest body leads to a chronic manifestation of intoxication and eventual mortality.

Slow release toxicant compositions, such as those taught in U.S. Pat. Nos. 3,639,583 and 3,417,181, rely upon release being affected through the now well-known and well-understood diffusion-dissolution mechanism. It is taught in said patents that release is critically dependent upon the binding polymeric matrix being a solute for the organotin classes used. The binder matrix is a vulcanized or a partially vulcanized elastomer. However, it is well known that generally organotins totally lack solubility in thermoplastic materials and, thus, the diffusion-dissolution process cannot be established.

In other inventions, it has been taught that the pesticidal agents such as organophosphorus class insecticides will similarly release from solute matrices, especially from elastomers. U.S. Pat. No. 3,590,119 is an example of this teaching.

Many mosquito larvicides are known and used in both the conventional sense as well as in controlled release methodologies such as microencapsulation. Among others, Boike et al has shown in examining 23 different organotins in solute elastomer formulations, that they are not effective against the mosquito under practical use situations due to the presence of natural organic substances common to water courses. Said organic materials rapidly absorb organotin molecules essentially removing them from mosquito larva contact.

U.S. Pat. No. 4,012,221 has taught that an elastomer insoluble toxicant, if said toxicant is highly water soluble and is present in relatively high matrix concentrations, can be made to release from said elastomer in excess of 75 parts by weight of toxic per 100 parts of elastomer.

U.S. Pat. No. 3,705,938 teaches that several organophosphorus-type insect adulticides can be incorporated in a laminated polyvinylchloride structure, wherein no agent solubility exists, and caused to move continuously through said plastic structure to said plastic surface through a volatility mechanism wherein the medium of release is air. Such constructions require the use of a third phase material such as a plasticizer to effect toxicant movement.

In pursuance of the invention described herein, it has been discovered that unlike conventional pesticides, specific organotin chemicals act through a hitherto unknown mechanism to effect mosquito and snail mortality. As is well known to the state of the art, organophosphorus, carbamate, halogenated hydrocarbon, and other organic materials affect mortality in insects by interference in vital enzyme systems. It is further well known that this mode of intoxication leads to the unwanted development of resistance to said chemicals through evolutionary processes. In contrast, organotin formulations described herein effect mortality through hitherto undiscovered physiological mechanisms that cannot induce tolerance in the target species.

SUMMARY OF THE INVENTION

Accordingly, it is an object of the present invention to provide a method and composition for destroying pest insects, usually in their aquatic stage, by utilizing essentially a water-insoluble organotin compound having no solubility in a thermoplastic matrix, but dispersed therein and caused to release upon contact with water through the use of a porosity enhancing coleachant of moderate to low water solubility.

It is an additional object of the present invention to provide a method and composition for destroying pest insects, as above, wherein said thermoplastic matrix is an ethylene-vinyl acetate polymer which possesses the ability to bind and release organotin compounds.

It is a further object of the present invention to provide a method and composition for destroying pest insects, as above, which is not harmful to non-target biota of the environment.

It is still an additional object of the present invention to provide a method and composition for destroying pest insects, as above, wherein said organotin compound is tributyltin fluoride.

It is still a further object of the present invention to provide a method and composition for destroying pest insects, as above, wherein a high mortality rate of said pest insects is produced.

These and other objects of the present invention will become apparent from the following specification describing in detail the preferred embodiment of the invention.

In general, a composition for destroying pests over a period of time, comprises: 100 parts of weight of a polymer matrix, said polymer matrix consisting essentially of an ethylene-vinyl acetate copolymer, the amount by weight of said ethylene constituent in said copolymer ranging from about 60 percent to about 92 percent; from about 25 parts to about 73 parts by weight per 100 parts of said copolymer matrix of a toxicant, said toxicant selected from the class consisting of a halogenated trialkyltin and a triaryltin; and from about 15 to about 70 parts by weight per 100 parts of said polymer matrix of a coleachant, said coleachant being an alkalin earth salt or an alkalin earth oxide having a solubility in water of 0.01 grams or less per 100 grams of water.

Generally, a method for destroying pests by the gradual and continuous release of an organotin toxicant from a thermoplastic matrix, comprises: preparing a mixture of the organotin toxicant, a polymer matrix, and a coleachant; the amount of said polymer matrix being 100 parts by weight, said polymer matrix consisting essentially of an ethylene-vinyl acetate copolymer, the amount by weight of said ethylene constituent in said copolymer ranging from about 60 percent to about 92 percent; the amount of said organotin toxicant ranging from about 25 parts to about 73 parts by weight per 100 parts of said polymer matrix, said organotin toxicant selected from the class consisting of a halogenated trialkyltin and a triaryltin; and from about 15 to about 70 parts by weight per 100 parts of said polymer matrix of a coleachant, said coleachant being an alkalin earth salt or an alkalin earth oxide having a solubility in water of 0.1 grams or less per 100 grams of water.

DESCRIPTION OF THE PREFERRED EMBODIMENT

The present invention relates to a sustained release composition containing a halogenated trialkyl organotin or a triaryl organotin which composition is very effective against mosquito larva and can also be utilized against molluscan hosts of various trematode parasites and, in some cases, the aquatic larval forms of such parasites, as well as other aquatic pests. The compositions involved permit a long duration controlled release of the said organotin in ultralow aggregate concentrations in water that result in the gradual accumulation of said agents within the responsive target pest tissues, chronic intoxication and eventual mortality. However, it is believed from empirical evidence that the halogenated trialkyl or triaryl organotins absorbed by or ingested by target species are both proteolytic and antimorphogenetic; and, because of the nature of such mechanisms leading to mortality for the target to acquire resistance would necessitate evolving new proteins and peptide linkages.

The pesticide composition consists of halogenated trialkyl organotin or a triaryl organotin possessing either low or very low water solubility and no thermoplastic solubility, bound and uniformly dispersed in a thermoplastic ethylene vinyl-acetate copolymer, wherein also uniformly dispersed is an inert material of moderate or low water solubility that serves a porosigenic function. The porosigen is a coleachant; but, unlike the elastomer-high toxicant system taught in U.S. Pat. No. 4,012,221, functions only to induce and enhance porosity within the matrix and has no function as an interfacial pH regulant. In the present invention, the organotin toxicant is monolithically dispersant in association with the porosity enhancing coleachant.

The halogenated organotin compounds of the present invention contain, preferably, an alkyl group having from 3 to 6 carbon atoms with butyl being highly preferred. The triaryl organotin compounds contain as an aryl group a substituted phenyl compound such as phenyl acetate, or esters or salts of 1,3,5-cyclohexatriene i.e., benzene, and the like.

The alkyl organotin compounds are halogenated with fluorine, chlorine, bromide, or iodine with fluorine being preferred. Thus, the preferred compound of the present invention is tributyltin fluoride. The solubility of the halogenated organotin compounds in a thermoplastic matrix or binder is nil, as noted, and very low in water; that is, approximately 30 parts per million by weight or less. The amount of halogenated organotin or aryl organotin compound utilized by weight per 100 parts of polymer matrix binding agent ranges from about 25 parts to about 73 parts, with from about 45 parts to 70 parts being preferred. Naturally, smaller or higher amounts may be utilized, but these ranges result in very effective pest-toxicant thermoplastic matrixes.

The polymer matrix or binding agent of the present invention relates to only ethylene-vinyl acetate copolymers since they have been found to possess the ability to bond and release halogenated organotin compounds. Such copolymers are readily available in commerce and the amount by weight of the ethylene repeating units, based upon the total weight of the copolymer, ranges from about 60 percent to about 95 percent with a range of from about 80 percent to about 92 percent being preferred. The molecular weight of the copolymer generally ranges from about 40,000 to about 300,000. Desirably, the copolymer has an ASTM Test No. D 1238 melt flow index of from about 7 to about 10 and a Vicat softening point of from about 70° to about 95° C. Since, apparently, the ethylene repeating units in the copolymer act as a regulator with regard to pore size, higher amounts of the ethylene constituent will result in slower release times. Moreover, in order to promote long release duration, it has been found useful, although not necessary, to blend the ethylene-vinyl acetate copolymer with a polyethylene, especially low density polyethylene, having a melt flow index similar to said ethylene-vinyl acetate copolymer and a molecular weight of from about 100,000 to about 400,000. Thus, depending upon the rate of release, various amounts of low density polyethylene may be utilized. Generally, to obtain desirable release rates, the amount of homopolyethylene utilized may range from about 30 percent to about 75 percent and, preferably, from about 40 percent to about 60 percent by weight, based upon the total weight of the blend of the ethylene-vinyl acetate copolymer and the polyethylene.

A number of moderate or low solubility compounds can be utilized as a porosity-inducing agent. By moderate or low solubility, it is meant that the solubility is 0.01 grams per 100 grams of water or less. The porosity-inducing agent or coleachant is generally an alkaline earth salt or oxide having low water solubility. Specific examples of coleachants include magnesium carbonate, magnesium bicarbonate, magnesium sulfate, magnesium nitrate, magnesium nitrite, magnesium phosphate, magnesium oxide, calcium carbonate, calcium bicarbonate, calcium sulfate, calcium nitrate, calcium nitrite, calcium phosphate; and, to a lesser desirability, barium carbonate, barium bicarbonate, barium sulfate, barium nitrate, barium nitrite, barium phosphate, barium oxide, beryllium carbonate, beryllium bicarbonate, beryllium sulfate, beryllium nitrate, beryllium nitrite, beryllium phosphate, and beryllium oxide. Calcium carbonate is highly preferred. The amount of coleachant generally varies from about 15 parts to about 70 parts by weight based upon 100 parts of said polymer matrix (that is, said copolymer or said blend of said polyethylene and said copolymer) and, preferably, from about 25 to about 60 parts.

The composition can contain, in addition to the above-mentioned necessary components, various well known and conventional additives to enhance dispersion, add color, aid in processing, or to alter the density. For example, should a composition be desired to sink, any composition having a specific gravity greater than 1 may be added in the necessary amounts to render the overall specific gravity of the material to be greater than 1. Naturally, a non-reactive, relatively inert and non-polluting or detrimental compound to the environment is desired such as silicon dioxide or the like. An example of a dispersant to aid in establishing a uniformed distribution of the organotins such as the tributyltin fluoride compound is zinc stearate in suitable amounts.

In order to form a suitable thermoplastic dispenser which releases suitable amounts of an organotin pesticide through a coleachant system, it is desirable that the particle sizes of the various components be relatively small. For example, it is desirable that the organotin compounds have a Tyler mesh size of roughly 200 or greater (i.e., a particle size smaller than 200 mesh). Accordingly, a particle size range for the coleachant is generally the same. The particle size of the ethylene-vinyl acetate copolymer or the blend of polyethylene and the ethylene-vinyl acetate copolymer is about 60 to 100 Tyler Mesh.

The pesticide is prepared by mixing the organotin compound with the polymer matrix and the coleachant in suitable proportions as indicated above in any conventional mixing apparatus along with various additives such as colorants, dispersants, and the like. The mixture is then coalesced by heating and is partitioned for use in any suitable size or shape, for example, pellet, chip, ribbon or ribbon form. For example, the mixture may be added to a conventional extruder where it is molded at about 170° C. to about 190° C. in a suitable form such as a rod, which may be cut up into appropriate pellet sizes. The invention will be better understood by reference to the following examples.

EXAMPLES

The components listed in Table I below were blended by roll mixing, adding the blend to the hopper of a conventional plastic extruder which was then extruded as a rod or a sheet of set dimensions. Since the release rate is proportional to the surface area, the surface of volume ratio is a major determinant of lifetime. Consequently, the extruded rod or sheet is commuted to a predetermined dimension commensurate with the desired biocidal lifetime.

TABLE I

|  | EXAMPLE 1 | EXAMPLE 2 | EXAMPLE 3 | EXAMPLE 4 |
|---|---|---|---|---|
|  | parts by Weight | | | |
| Ethylene-vinyl acetate copolymer | 56.2 | 28.6 | 22.0 | 43.0 |
| Polyethylene | — | 27.6 | 22.0 | — |
| Zinc Stearate | 2.4 | 2.4 | 1.0 | 2.0 |
| Calcium Carbonate | 17.0 | 17.0 | 25.0 | 17.0 |
| Silicon dioxide | — | — | — | 8.0 |
| Tributyltin fluoride | 24.4 | 24.4 | 30.0 | 30.0 |

The ethylene-vinyl acetate copolymer was Microthene MU 763 (9 percent vinyl acetate) having a melt flow index of 9.0 grams per 10 minutes according to ASTM Test No. D 1238 and can be a similar material. Zinc stearate, silicon dioxide and calcium carbonate must be finely divided particles of 200 or greater mesh size for adequate dispersion. The low density polyethylene material was Microthene MN 718 having a melt flow index of 8.5, although Microthene MN 786 having a melt flow index of 8.6, or a similar material can be used. (Microthene is the trademark of U.S.C. Chemicals of New York, New York).

Example 1 above is a fast-release floating material useful in vegetatively overgrown stagnant water, or as an anchored ribbon in catch basins or similar mosquito breeding sites wherein periodic flushing with water would normally wash away a pellet or granule. Example 2 is a slow release material which floats due to its low density. Example 3 is a slow-release sinking material and Example 4 is a fast-release sinking composition. It has also been observed that release is not molecular, as seen with elastomer binding matrices, but rather the organotin leachant is an aggregate of molecules whose cohesiveness or attraction to each other is dramatically greater than their attraction to suspended or dissolved natural organic constituents of water so that combination and effective detoxification proceeds at a relatively slow rate.

Materials such as those shown in Table I have been examined in periodic challenge bioassay and the $LT_{100}$ (lethal time to 100 percent population mortality) determined, using the larvae Culicine mosquito species as the test animal. Table II is a compendium of values for Formulation No. 3 (Example 3).

TABLE II

FORMULATION NO. 3
-VS- Culex Pipiens Quinquefasciatus LARVA
(First and Second Instar)[1]

| Total Available Agent[2] (ppm) | Immersion Time (days) | $LT_{100}$ (days) | Immersion Time (days) | $LT_{100}$ (days) | Immersion Time (days) | $LT_{100}$ (days) |
|---|---|---|---|---|---|---|
| 12.5 | 30 | 2 | 106 | 4 | 160 | 4 |
| 8.0 | 30 | 3 | 106 | 9 | 160 | 8 |
| 4.1 | 30 | 7 | 110 | 13 | 160 | 12 |
| 2.7 | 30 | 8 | 106 | 13 | 160 | — |
| 2.3 | 30 | 10 | 110 | 4 | 160 | 8 |
| 1.4 | 30 | 10 | 110 | 13 | 160 | 11 |
| 0.47 | 30 | 8 | 110 | 13 | 160 | 12 |
| 12.5 | 225 | 5 | 310 | 12 | | |
| 8.0 | 225 | 7 | 310 | 13 | | |
| 4.1 | 225 | 9 | 310 | 13 | | |
| 2.7 | 225 | 10 | 310 | 15 | | |
| 2.3 | 225 | 12 | 310 | * | | |
| 1.4 | 225 | 12 | 310 | * | | |

TABLE II-continued

FORMULATION NO. 3
-VS- Culex Pipiens Quinquefasciatus LARVA
(First and Second Instar)[1]

| Total Available Agent[2] (ppm) | Immersion Time (days) | $LT_{100}$ (days) | Immersion Time (days) | $LT_{100}$ (days) | Immersion Time (days) | $LT_{100}$ (days) |
|---|---|---|---|---|---|---|
| 0.47 | 225 | 10 | 310 | * | | |

[1]Seventy-five mosquito larvae in five separate containers were bioassayed at each concentration. Pellets are continuously immersed with periodic water change between tests.
[2]Total available agent refers to the amount within the pellets, prior to immersion, and not to the water concentration.

The threshold tributyltin fluoride release rate is approximately 0.0097 parts-per-million per day.

Long term results, from another bioassay series, are shown in Table III.

TABLE III

FORMULATION NOS. 2 and 3 -VS- CULICINE LARVA
(First and Second Instars)

| Formulation | Agent (ppm) | Time (days) | $LT_{100}$ (days) | Percent Pupation | Percent Adult |
|---|---|---|---|---|---|
| No. 2 | 30.2 | 481 | 7 | 0 | 0 |
| | 16.3 | 481 | 5 | 0 | 0 |
| | 6.9 | 470 | 10 | 7 | 0 |
| | 4.3 | 470 | 16 | 20 | 0 |
| | 1.95 | 495 | 16 | 20 | 0 |
| No. 3 | 32.6 | 407 | 5 | 0 | 0 |
| | 16.3 | 473 | 5 | 0 | 0 |
| | 5.94 | 483 | 11 | 0 | 0 |
| | 5.61 | 512 | 10 | 0 | 0 |
| | 5.22 | 485 | 8 | 0 | 0 |
| | 5.19 | 497 | 15 | 13 | 0 |
| | 4.80 | 492 | 14 | 0 | 0 |
| | 2.46 | 473 | 15 | 40 | 0 |
| | 1.92 | 485 | 15 | 13 | 7 |
| | 0.92 | 485 | 16 | 13 | 13 |

Several salient features were observed that contributed to the uniqueness of this sytem. Unlike almost all conventionally used mosquito larvicides, these substances are effective pupacides. Also, morphogenetic damage was dramatically evident. In the normal sequence of events, morphogenesis from instar to instar occurs at one, two, or three-day intervals for the four larval instars characteristic of the test species. In general, such changes did not occur. For instance, second instar larva remained at that stage of development for up to 13 days, whereas normal metamorphosis to the third instar would occur in two or three days.

In bioassay measurements against molluscs in general and *Biomphalaria glabrata* males in particular, effective biocidal action is noted using the subject invention. It is well known to the state-of-the-art that various organotin agents, including tributyltin fluoride can be released from elastomeric materials with efficacious molluscicidal activity seen. Heretofore, it has not been possible to utilize plastic materials in this usage and indeed the state-of-the-art has believed that effective release of organotins from nonsolute polymers such as plastics could not be achieved.

Long term results using the formulations given above have been observed in bioassay against said snails as shown in Table IV. It is noted that *Biophalaria glabrata* is a major host snail for the Schistosoma mansoni parasite, the causative agent for the dreaded major human disease, "Schistosomiasis".

TSBLE IV

FORMULATIONS 2 and 3 -VS- ADULT *BIOMPHALARIA GLABRATA* SNAILS
(5 replicates × 10 snails/replicate)

| Formulation | Total Available Agent (ppm) | Immersion Time (days) | $LT_{100}$ (days) | Immersion Time | $LT_{100}$ (days) | Immersion Time | $LT_{100}$ (days) |
|---|---|---|---|---|---|---|---|
| No. 2 | 10 | 0 | 4 | 60 | 10 | 120 | 12 |
| | 5.4 | 0 | 6 | 60 | 11 | 120 | 21 |
| | 2.3 | 0 | 7 | 60 | 19 | 120 | 40 |
| | 1.4 | 0 | 8 | 60 | 24 | 120 | — |
| | 0.6 | 0 | 12 | 60 | 28 | 120 | — |
| | 10 | 240 | 15 | | | | |
| No. 3 | 12.5 | 0 | 4 | 60 | 7 | 120 | 9 |
| | 8.2 | 0 | 6 | 60 | 8 | 120 | 10 |
| | 2.0 | 0 | 8 | 60 | 9 | 120 | 17 |
| | 1.9 | 0 | 8 | 60 | 11 | 120 | 21 |
| | 1.7 | 0 | 9 | 60 | 15 | 120 | 22 |
| | 1.7 | 0 | 9 | 60 | 15 | 120 | 24 |
| | 1.6 | 0 | 9 | 60 | 17 | 120 | 26 |
| | 0.8 | 0 | 12 | 60 | 19 | 120 | 30 |
| | 0.6 | 0 | 14 | 60 | 22 | 120 | 35 |
| | 12.5 | 240 | 8 | | | | |
| | 8.2 | 240 | 11 | | | | |
| | 4.1 | 240 | 14 | | | | |
| | 2.3 | 240 | 22 | | | | |

In biassay tests against both larva forms of the *Schistosoma mansoni* schistosome, it is observed that extremely low toxicant levels are effective (Table V).

TABLE V

FORMULATIONS 2 and 3 -VS- SCHISTOLARVA

| Formulaton | Total Avalable Toxicant (ppM) | $LT_{100}$ (min) Miracidia | $LT_{100}$ (min) Cercariae |
|---|---|---|---|
| No. 2 | 0.008 | 60 | 60 |
| | 0.0008 | 180 | 120 |
| | 0.00008 | 240 | 480 |
| No. 3 | 0.008 | 60 | 60 |
| | 0.0008 | 60 | 120 |
| | 0.00008 | 240 | 480 |

Although the $LT_{100}$ is considered the indicium of effectiveness, it is noted that larvae mobility ceases in a shorter duration and the cercarial form loses the ability to infect a susceptible host in still less time. It is, thus, postulated that unlike conventional materials of a mollusicidal or cercariacidal nature, long lasting formulations, as reported herein, can be effectively used in ultra low concentrations as a means of intervening the Schistosomiasis transmission cycle, thus, offering substantial protection to humans contacting the infested waters.

The use of toxic materials against target pests often results in ecological damage through concomitant effects upon nontarget biota. Environmental impact and toxicity tests using the four formulations of Table I indicate a relatively low effect on various life forms associated with the aquatic habitat. Floating aquatic plants such a Lemna (duckweek) and *Eichornia crassipes* (water hyacinth) are unaffected in thirty-day bioassay evaluations. In contrast, *Elodea canadensis,* when rooted, is susceptible to intoxication at 10 ppm and 1 ppm dosages. Micro-organisms such as monocellular green algae and other phytoplankters show relatively little population suppression and the effects seen are reversible after thirty to sixty days post exposure. Field reports have confirmed laboratory studies. Fish are unaffected at 10 ppm total active concentrations as shown in standard bioassay using *Lebistes reticulatus* as a moderately susceptible fish species. In mouse toxicity and teratogenicity studies, no gross physciological or behavior effects are noted over four generations, whose water supply was treated with Formulation 3 at 10 ppm. Rats fed Formulation 3, using standard toxicity tests, indicate a mamalian $LD_{50}$ in excess of 2,000 mg/kg.

While in accordance with the patent statutes, the best mode and preferred embodiment has been described in detail, the invention is to be measured by the appended claims.

What is claimed is:

1. A composition for destroying aquatic pests over a period of time, comprising:
   100 parts by weight of a polymer matrix, said polymer matrix consisting essentially of an ethylene-vinyl acetate copolymer, the amount by weight of said ethylene constituent in said copolymer ranging from about 60 percent to about 92 percent, the molecular weight of said ethylene-vinyl acetate copolymer ranging from about 40,000 to about 300,000;
   from about 25 parts to about 73 parts by weight per 100 parts of said copolymer matrix of a toxicant, said toxicant selected from the class consisting of a halogenated trialkyltin and a triaryltin, said alkyl group of said halogenated trialkyltin compound containing from 3 to 6 carbon atoms and said aryl group of said triaryltin being selected from the class consisting of a substituted phenyl, esters of benzene, and salts of benzene; and
   from about 15 to about 70 parts by weight per 100 parts of said polymer matrix of a porosity inducing agent, said porosity inducing agent being an alkaline earth salt or an alkaline earth oxide having a medium to low solubility in water of 0.01 grams or less per 100 grams of said water.

2. A composition according to claim 1, wherein said porosity inducing agent has an anion portion and a cation portion, said cation portion selected from the class consisting of beryllium, magnesium, calcium and barium, and said anion portion selected from the class consisting of carbonate, bicarbonate, sulfate, nitrate, nitrite, phosphate, and oxide.

3. A composition according to claim 2, wherein said toxicant is tributyltin fluoride.

4. A composition according to claim 3, wherein said porosity inducing agent is calcium carbonate.

5. A composition according to claim 3 or 4, wherein the amounts of said toxicant ranges from about 45 parts to about 70 parts by weight and the amount of porosity inducing agent ranges from about 25 parts to about 60 parts by weight, and wherein the melt flow index of said copolymer is from about 7 to about 10.

6. A composition according to claim 5, wherein the amount of said ethylene constituent of said copolymer ranges from about 80 percent to about 92 percent.

7. A composition according to claim 2, wherein said 100 parts of said polymer matrix contains from about 25 parts to about 70 parts by weight of said ethylene-vinyl acetate copolymer and further including from about 75 parts to about 30 parts by weight of a low density polyethylene having a molecular weight of from about 100,000 to about 400,000.

8. A composition according to claim 5, wherein said 100 parts of said polymer matrix contains from about 25 to about 70 parts by weight of said ethylene-vinyl acetate copolymer, and further including from about 75 parts to about 30 parts by weight of a low density polyethylene having a melt flow index of from about 7 to about 10.

9. A composition according to claim 8, wherein said polyethylene has a molecular weight of from about 100,000 to about 400,000 and wherein said polymer matrix contains from about 40 parts to about 60 parts by weight of said ethylene-vinyl acetate copolymer and the amount of said low density polyethylene polymer ranges from about 60 parts to about 40 parts by weight.

10. A method for destroying aquatic pests by the gradual and continuous release of an organotin toxicant from a thermoplastic matrix, comprising applying said aquatic pest composition of claim 1 to an aquatic environment.

11. A method according to claim 10, wherein said porosity inducing agent has a cation portion and an anion portion, said cation portion selected from the class consisting of beryllium, magnesium, calcium, and barium, and said anion portion selected from the class consisting of carbonate, bicarbonate, sulfate, nitrate, nitrite, phosphate, and oxide.

12. A method according to claim 11, wherein said organotin toxicant is tributyltin fluoride and said porosity inducing agent is calcium carbonate.

13. A method according to claim 12, including placing said matrix into an appropriate aquatic environment for destroying aquatic larva stages of parasitic flatworms, for destroying mollusc hosts of parasitic flatworms, and for destroying mosquito larva.

14. A method according to claim 12, wherein the amount of said toxicant ranges from about 45 parts to about 70 parts by weight and the amount of said porosity inducing agent ranges from about 25 parts to about 60 parts by weight;
   wherein the amount of said ethylene constituent of said copolymer ranges from about 80 percent to about 92 percent; and
   wherein the melt flow index of said copolymer is from about 7 to about 10.

15. A method according to claim 11 or 12, wherein said 100 parts of said polymer matrix contains from about 25 to about 70 parts by weight of said ethylene-vinyl acetate copolymer and further including from about 75 to about 30 parts by weight of a low density polyethylene.

16. A method according to claim 14, wherein said 100 parts of said polymer matrix contains from about 25 to about 70 parts by weight of said ethylene-vinyl acetate copolymer and further including from about 75 to about 30 parts by weight of a low density polyethylene having a melt flow index of from about 7 to about 10.

17. A method according to claim 16, wherein said polyethylene, has a molecular weight of from about 100,000 to about 400,000, wherein said polymer matrix contains from about 40 parts to about 60 parts by weight of said ethylene-vinyl acetate copolymer and the amount of said low density polyethylene polymer ranges from about 60 parts to about 40 parts by weight.

18. A method according to claim 11, or claim 12, or claim 14, or claim 16, wherein said organotin toxicant is monolithically dispersed within said polymer matrix.